(12) United States Patent
Stoltefuss et al.

(10) Patent No.: US 6,699,857 B1
(45) Date of Patent: Mar. 2, 2004

(54) TETRAHYDROQUINOLINYL 6-METHYLDIHYDROTHIADIAZINONE DERIVATIVES AND USE THEREOF

(75) Inventors: Jürgen Stoltefuss, Haan (DE);
Gabriele Bräunlich, Wuppertal (DE);
Michael Lögers, Wuppertal (DE);
Carsten Schmeck, Wuppertal (DE);
Ulrich Nielsch, Düsseldorf (DE);
Martin Bechem, Wuppertal (DE);
Christoph Gerdes, Leverkusen (DE);
Michael Sperzel, Wuppertal (DE);
Klemens Lustig, Wuppertal (DE);
Werner Stürmer, Stockach (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 10/018,928

(22) PCT Filed: Jun. 16, 2000

(86) PCT No.: PCT/EP00/05571
§ 371 (c)(1),
(2), (4) Date: Apr. 1, 2002

(87) PCT Pub. No.: WO01/00188
PCT Pub. Date: Jan. 4, 2001

(30) Foreign Application Priority Data

Jun. 29, 1999 (DE) .......................... 199 29 785

(51) Int. Cl.⁷ ............................. A61K 31/541
(52) U.S. Cl. ................................. 514/222.5
(58) Field of Search .................. 544/8; 514/222.5

(56) References Cited

U.S. PATENT DOCUMENTS

| | | | |
|---|---|---|---|
| 4,916,128 A | 4/1990 | Jonas et al. | 514/213 |
| 5,137,885 A | 8/1992 | Jonas et al. | 514/225 |
| 5,206,363 A | 4/1993 | Jonas et al. | 540/593 |

FOREIGN PATENT DOCUMENTS

| | | |
|---|---|---|
| DE | 4230755 | 3/1994 |
| DE | 4338948 | 5/1995 |
| EP | 0721950 | 6/1998 |

OTHER PUBLICATIONS

Abstr. Bd. 24, Nr. Suppl. 2, 1994, Seit A5: XP–000972326, Schwinger, R., Bohm, M., Uhlmann, R., Lues, I., Erdmann, E., "Enantioselective Ca²+Sensitizing Effects of EMD 53998, EMD 57033 and EMD 57439 in Himan Myocardium" (1994).

Devant, R., Jonas, R., Schulte, M., Keil, A., Charton, F., "Enantiomer Separation of a Novel Ca–Sensitizing Drug by Simulated Moving Bed (SMB)—Chromatography", J. prakt. Chem., 339:315–321 (1997).

Eckardt, K., "Erythropoietin: Karriere eines Hormons", Deutsches Arzteblatt, 95: A–285–A290 (1998).

Pschyrembel, Klinisches Worterbuch, Walter de Gruyter, Berlin.New York 2002, 1994, pp. 64–67.

Puhler, Regitz & Schmid, Rompp Lexikon Chemie, ver. 1.5, Georg Thieme Verlad, Stuttgart. New York, 1998, p. 33.

Roche–Lexikon Medizin, 4, Auflage, Urban & Schwarzenberg, 1999.

Kuschinsky, Lullmann & Peters, Kurzes Lehrbuch der Pharmakologie und Toxikologie, 9, Auflage, Georg Thieme Verlag Stuttgart, 1981, pp. 139–142.

Mutschler, Lehrbuch der Pharmakologie und Toxikologie, Wissenschaftliche Verlagsgesellschaft mbH Stuttgart, 1986, pp. 383–389.

Rote Liste 2000, Editio Cantor Verlag, Aulendorf, 2000, "Epoetin alfa" und "Epoetin beta".

*Primary Examiner*—John M. Ford

(57) ABSTRACT

The invention relates to the area of erythropoiesis, in particular to the use of tetrahydroquinolinyl-6-methyldihydrothiadiazinones of general formula (I) for treating anaemia.

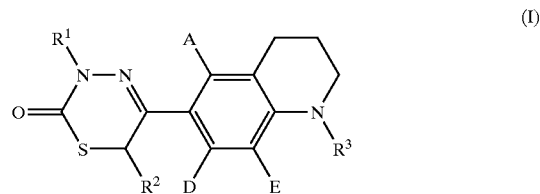

The invention also relates to novel tetrahydroquinolinyl-6-methyldihydrothiadiazinone derivatives and to the production thereof.

19 Claims, No Drawings

TETRAHYDROQUINOLINYL 6-METHYLDIHYDROTHIADIAZINONE DERIVATIVES AND USE THEREOF

The present invention relates to the field of erythropoiesis. In particular, the present invention relates to the use of tetrahydroquinolinyl-6-methyldihydrothiadiazinones for the prophylaxis and/or treatment of anaemias. Novel tetrahydroquinolinyl-6-methyldihydrothiadiazinone derivatives, and their preparation, are also described.

Anemias are characterized by the erythrocyte count, hemoglobin concentration and/or hematocrit decreasing below the age-related and sex-specific reference values. However, a decrease in one of these parameters is only a sign of an anemia when the blood volume is normal but not when the decrease is associated with acute, relatively marked blood losses, exsiccosis (pseudopolyglobulism) or hydremia (pseudoanemia). (Pschyrembel, Klinisches Wörterbuch [Clinical Dictionary], 257th edition, 1994, Walter de Gruyter Verlag, page 59 ff., entry "Anemia"; Römpp Lexikon Chemie [Römpp Chemistry Encyclopedia], version 1.5, 1998, Georg Thieme Verlag Stuttgart, entry "Anemia").

As a consequence of the decreased capacity of the blood to transport oxygen, anemia is characterized clinically by, inter alia, disturbances in oxygen-dependent metabolism and organ functions; when the anemia develops acutely, for example as a consequence of the loss of blood, shock symptoms can appear, and, when it develops chronically, there is frequently a slowly progressing course associated with decline in performance, tiredness, dyspnea and tachycardia.

The different forms of anemia can be subdivided or classified either in accordance with the morphology and hemoglobin content of the erythrocytes or in accordance with etiology (for example into posthemorrhagic anemia, pregnancy anemia, tumor anemia, infection anemia and deficiency anemias). It is furthermore possible to subdivide the different forms of anemia in accordance with their pathogenesis while taking into consideration the causes which are in principle possible, for example into anemias caused by excessive loss of blood (for example acute or chronic hemorrhagic anemia), anemias resulting from reduced or ineffective erythropoiesis (for example iron deficiency anemias, nephrogenic anemias or myelopathic anemias) and anemias resulting from excessive erythrocyte breakdown (what are termed hemolytic anemias) (Pschyrembel, Klinisches Wörterbuch, 257th edition, 1994, Walter de Gruyter Verlag, page 59 ff., entry "anemia"; Roche-Lexikon Medizin [Roche Medical Encyclopedia], 4th edition, 1999, Urban & Schwarzenberg, entry "anemia").

In practice, the methods for treating anemias which are disclosed in the prior art prove to be very difficult and not particularly efficient. Large numbers of side-effects, which are frequently serious to the patient, usually occur.

Thus, in the therapy of iron deficiency anemias, use is generally made of iron preparations which are administered either orally or parenterally. When they are administered orally, it is, in particular, gastrointestinal disturbances which are observed as side-effects. The simultaneous administration of antacids, for the purpose of treating the gastrointestinal disturbances, impairs absorption of the iron. Furthermore, the absorption of iron from the intestinal tract is in any case only very limited because of the ability of the mucosa to impede the passage of iron. On the other hand, a dose which is administered orally should not be too high because, if it is, symptoms of poisoning can then occur, in the worst case even a hemorrhagic gastroenteritis which is associated with shock symptoms and leads to death. Administration of the iron therapy parenterally, which likewise proves to be difficult because of the plasma only having a low ability to bind iron, can lead, particularly when an overdose is given, to nausea, vomiting, cardialgias and headaches, heat sensations and a severe fall in blood pressure associated with collapse, and, furthermore, to the deposition of iron in the reticuloendothelium (hemosiderosis); the blood vessel walls are damaged by the intravenous injection and thrombophlebitis and clot formation must be expected. Dosing proves to be extremely difficult since all the iron which cannot be bound physiologically when it is administered parenterally then has a toxic effect (Gustav Kuschinsky, Heinz Lüllmann and Thies Peters, Kurzes Lehrbuch der Pharmakologie und Toxikologie [Short Textbook of Pharmacology and Toxicology], 9th edition, 1981, Georg Thieme Verlag Stuttgart, pages 139 ff.; Ernst Mutschler, Arzneimittelwirkungen, 30 Lehrbuch der Pharmakologie und Toxikologie [Effects of Medicaments, Textbook of Pharmacology and Toxicology], Wissenschaftliche Verlagsgesellschaft mbH Stuttgart, 1986, pages 383 ff.).

For somewhat more than 10 years now, recombinant erythropoietin (rhEPO), 35 which is prepared by genetic manipulation, has been available for therapeutic employment for treating severe anemias. This is because, it is known that recombinant human (rh) EPO stimulates erythropoiesis humorally, as a result of which it has come to be used as an antianemic agent in the therapy of severe anemias, particularly in renal and nephrogenic anemias. In addition, rh EPO is used for increasing the number of endogenous blood cells in order to decrease the requirement for transfusions of foreign blood.

Erythropoietin (EPO) is a glycoprotein which has a molecular weight of about 34 000 Da. More than 90% of the EPO is synthesized in the kidney, and the EPO which is produced in this organ is secreted into the blood. The primary physiological function of EPO is that of regulating erythropoiesis in the bone marrow. In this location, EPO stimulates the proliferation and maturation of the erythrocytic precursor cells.

However, powerful side-effects occur when rh EPO is administered. These side effects include the development and amplification of high blood pressure and the causation of an encephalopathy-like symptomatology, leading all the way to tonic/clonic convulsions and cerebral or myocardial infarction due to thromboses. Furthermore, rh EPO is not available orally and has therefore to be administered intraperitoneally (i.p.), intravenously (i.v.) or subcutaneously (s.c.), thereby restricting its use to the therapy of severe anemias (Kai-Uwe Eckardt, "Erythropoietin: Karriere eines Hormons" [Career of a Hormone], Deutsches [Career of a Hormone], Deutsches Ärzteblatt 95, issue 6 dated Feb. 6, 1998 (41), pages A-285 to A-290; Rote Liste [Red List] 1998, Editio Cantor Verlag für Medizin und Naturwissenschaften GmbH, see "Epoetin alpha" and "Epoetin beta").

The publications EP 721 950, DE 42 30 755 and DE 43 38 948 disclose various quinolylthiadiazin-2-one-3-carboxylates which have a cardiovascular effect.

In addition the publication J. Prakt. Chem. Chem.-Ztg. (1997), 339 (4), 315–321 has described the enantiomeric resolution to give the (+)-3,6-dihydro-6-methyl-5-(1,2,3,4-tetrahydro-6-quinolinyl)-2H-1,3,4-thiadiazin-2-one.

An object of the present invention is now to find substances which are particularly suitable for treating anemias more efficiently and which, at the same time, avoid the disadvantages of the methods for treating anemias which are known from the prior art.

Another object of the present invention is that of providing novel compounds for the abovementioned purpose and also a process for preparing them.

It has now been found, surprisingly, that the compounds of the general formula (I)

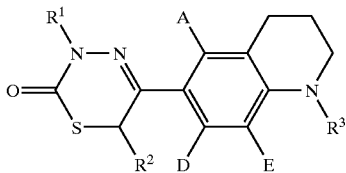

in which
  A, D and E are identical or different and represent hydrogen, halogen, trifluoromethyl or hydroxyl or represent $(C_1-C_6)$-alkyl or represent $(C_1-C_6)$-alkoxy,
  $R^1$ and $R^2$ are identical or different and represent hydrogen or represent $(C_1-C_6)$-alkyl, in particular represent $(C_1-C_4)$-alkyl,
  $R^3$ represents a radical of the formula $-(X)_a-R^4$,
    in which
    X represents CO or $SO_2$,
    a denotes a number 0 or 1,
    and
    $R^4$ denotes $(C_3-C_8)$-cycloalkyl or $(C_6-C_{10})$-aryl or a 5- to 6-membered aromatic heterocycle having up to 3 ring heteroatoms from the series S, N and/or O, it being possible for the ring systems which are listed here to be optionally substituted up to 3 times, identically or differently, by substituents selected from the group consisting of: halogen, trifluoromethyl, nitro, hydroxyl, carboxyl, $(C_1-C_6)$-alkyl, $(C_1-C_6)$-alkoxy and $(C_1-C_6)$-alkoxycarbonyl,
    or
    $R^4$ denotes $(C_1-C_8)$-alkyl which is optionally substituted by $(C_6-C_{10})$-aryl, phenoxy or benzyloxy or by a 5- to 6-membered aromatic heterocycle having up to 3 ring heteroatoms form the series S, N and/or O, it being possible for the ring systems which are listed here to be optionally substituted, up to 4 times, identically or differently, by substituents selected from the group halogen, nitro, trifluoromethyl, cyano, carboxyl, hydroxyl, trifluoromethoxy, $(C_1-C_6)$-alkylthio, $(C_1-C_6)$-alkoxy and $(C_1-C_6)$-alkoxycarbonyl,
    or
    $R^4$ denotes a radical of the formula $-CO-NR^5R^6$,
      in which
      $R^5$ and $R^6$ are identical or different and denote hydrogen or $(C_1-C_6)$-alkyl which is optionally substituted by $(C_6-C_{10})$-aryl which, for its part, can be substituted, once to twice, identically or differently, by halogen or $(C_1-C_6)$-alkyl, or denote $(C_6-C_{10})$-aryl which can be optionally substituted, once to three times, identically or differently, by halogen, nitro, cyano, $(C_1-C_6)$-alkyl, $(C_1-C_6)$-alkoxy or hydroxyl,
and the salts thereof,
are suitable for the prophylaxis and/or treatment of anaemia's.

Depending on the substitution pattern, the compounds according to the invention can exist in stereoisomeric forms which either relate to each other as image and mirror image (enantiomers) or which do not relate to each other as image and mirror image (diastereomers). The invention relates both to the enantiomers or diastereomers and to their respective mixtures. The racemic forms, like the diastereomers, can be resolved, in a known manner, into the stereoisomerically uniform constituents.

Physiologically harmless salts of the compounds according to the invention can be salts of the substances according to the invention with mineral acids, carboxylic acids or sulfonic acids. Particular preference is given, for example, to salts with hydrochloric acid, hydrobromic acid, sulfuric acid, phosphoric acid, methanesulfonic acid, ethanesulfonic acid, toluenesulfonic acid, benzenesulfonic acid, naphthalenedisulfonic acid, acetic acid, propionic acid, lactic acid, tartaric acid, citric acid, fumaric acid, maleic acid or benzoic acid.

Salts which may be mentioned are also salts with customary bases, for example alkali metal salts (e.g. sodium or potassium salts), alkaline earth metal salts (e.g. calcium or magnesium salts) or ammonium salts derived from ammonia or organic amines such as diethylamine, triethylamine, ethyldiisopropylamine, procaine, dibenzylamine, N-methylmorpholine, dihydroabietylamine, 1-ephenamine or methylpiperidine.

$(C_3-C_8)$-Cycloalkyl represents cyclopropyl, cyclopentyl, cyclobutyl, cyclohexyl, cycloheptyl or cyclooctyl. Cyclopropyl, cyclopentyl and cyclohexyl may be mentioned as being preferred.

$(C_6-C_{10})$-Aryl generally represents an aromatic radical having from 6 to 10 carbon atoms. Preferred aryl radicals are phenyl and naphthyl.

$(C_1-C_8)$-Alkyl, $(C_1-C_6)$-alkyl, or $(C_1-C_4)$-alkyl represent a straight-chain or branched alkyl radical having from 1 to 8, 1 to 6 or 1 to 4 carbon atoms. Examples which may be mentioned are: methyl, ethyl, n-propyl, isopropyl, n-butyl, isobutyl, tert-butyl, n-pentyl and n-hexyl. A straight-chain or branched alkyl radical having from 1 to 4 carbon atoms is preferred. A straight-chain or branched alkyl radical having from 1 to 3 carbon atoms is particularly preferred.

$(C_1-C_6)$-Alkoxy represents a straight-chain or branched alkoxy radical having from 1 to 6 carbon atoms. Examples which may be mentioned are: methoxy, ethoxy, n-propoxy, isopropoxy, n-butoxy, isobutoxy, tert-butoxy, n-pentoxy and n-hexoxy. A straight-chain or branched alkoxy radical having from 1 to 4 carbon atoms is preferred. A straight-chain or branched alkoxy radical having from 1 to 3 carbon atoms is particularly preferred.

$(C_1-C_6)$-Alkoxycarbonyl represents a straight-chain or branched alkoxycarbonyl radical having from 1 to 6 carbon atoms. Examples which may be mentioned are: methoxycarbonyl, ethoxycarbonyl, n-propoxycarbonyl, isopropoxycarbonyl, n-butoxycarbonyl, isobutoxycarbonyl and tert-butoxycarbonyl. A straight-chain or branched alkoxycarbonyl radical having from 1 to 4 carbon atoms is preferred. A straight-chain or branched alkoxycarbonyl radical having from 1 to 3 carbon atoms is particularly preferred.

A 5- to 6-membered aromatic heterocycle having up to 3 heteroatoms from the series S, O and/or N represents, for example, pyridyl, pyrimidyl, pyridazinyl, thienyl, furyl, pyrrolyl, thiazolyl, oxazolyl or imidazolyl. Pyridyl, thienyl, pyridazinyl, furyl and thiazolyl are preferred.

$(C_1-C_6)$-alkylthio represents a straight-chain or branched alkylthio radical having from 1 to 6 carbon atoms. Examples which may be mentioned are: methylthio, ethylthio, propylthio and butylthio. A straight-chain or branched alkylthio radical having from 1 to 4 carbon atoms is preferred. A straight-chain or branched alkylthio radical having from 1 to 3 carbon atoms is particularly preferred.

A 5- to 6-membered aromatic heterocycle having up to 3 heteroatoms from the series S, O and/or N represents, for example, pyridyl, pyrimidyl, pyridazinyl, thienyl, furyl, pyrrolyl, thiazolyl, oxazolyl or imidazolyl. Pyridyl, pyrimidyl, pyridazinyl, furyl and thienyl are preferred.

Preference is given to using, for the prophylaxis and/or treatment of anaemias, the compounds of the general formula (I),
in which
A, D and E are identical or different and represent hydrogen, fluorine, chlorine, bromine or hydroxyl, or represent $(C_1–C_4)$-alkyl or represent $(C_1–C_4)$-alkoxy,
$R^1$ and $R^2$ are identical or different and represent hydrogen, methyl or ethyl,
$R^3$ represents a radical of the formula $—(X)_a—R^4$,
in which
X represents CO or $SO_2$,
a denotes a number 0 or 1,
and
$R^4$ denotes cyclopropyl, cyclopentyl, cyclohexyl or cyclohepyl, or denotes phenyl, phenoxy, benzyloxy, naphthyl, pyridyl, pyrimidyl, pyridazinyl, thienyl, furyl, imidazolyl or pyrryl which can each be optionally substituted, up to 3 times, identically or differently, by substituents selected from the group fluorine, chlorine, bromine, $(C_1–C_4)$-alkyl, $(C_1–C_4)$-alkoxy and hydroxyl,
or
$R^4$ denotes $(C_1–C_6)$-alkyl which is optionally substituted by phenyl, phenoxy, naphthyl, pyridyl, pyrimidyl, pyridazinyl, thienyl or furyl, which, for their part, can optionally be substituted, up to 4 times, identically or differently, by substituents selected from the group fluorine, chlorine, bromine, nitro, trifluoromethyl, cyano, tri fluoromethoxy, hydroxyl, $(C_1–C_4)$-alkoxy and $(C_1–C_4)$-alkyl,
or
$R^4$ denotes a radical of the formula $—CO—NR^5R^6$,
in which
$R^5$ and $R^6$ are identical or different and denote hydrogen or denote $(C_1–C_4)$-alkyl which is optionally substituted by phenyl or fluorine, or denote naphthyl or phenyl which are each optionally substituted, up to 2 times, identically or differently, by fluorine, chorine or $(C_1–C_3)$-alkyl,
and the salts thereof.

Particular preference is given to using, for the prophylaxis and/or treatment of anaemias, the compounds of the general formula (I)
in which
A, D and E are identical or different and represent hydrogen, fluorine, chlorine or $(C_1–C_3)$-alkyl,
$R^1$ and $R^2$ are identical or different and represent hydrogen or methyl,
$R^3$ represents a radical of the formula $—(X)_a—R^4$,
in which
X represents CO or $SO_2$,
a denotes a number 0 or 1,
and
$R^4$ denotes cycloalkyl or cyclohexyl or denotes phenyl or pyridyl which can each be optionally substituted, up to 2 times, identically or differently, by substituents selected from the group fluorine, chlorine, bromine, $(C_1–C_3)$-alkyl and $(C_1–C_4)$-alkoxy,
or
$R^4$ denotes $(C_1–C_4)$-alkyl which is optionally substituted by phenyl, pyridyl, pyrimidyl or pyridazinyl which are each optionally substituted, up to 2 times, identically or differently, by substituents selected from the group fluorine, chorine, bromine, nitro, cyano, hydroxyl, trifluoromethyl, trifluoromethoxy, $(C_1–C_3)$-alkylthio, $(C_1–C_3)$-alkyl and $(C_1–C_3)$-alkoxy,
or
$R^4$ denotes a radical of the formula $—CO—NR^5R^6$,
in which
$R^5$ and $R^6$ are identical or different and denote hydrogen or
denote $(C_1–C_3)$-alkyl which is optionally substituted by phenyl or fluorine or
denote phenyl or naphthyl which are each optionally substituted, once to twice, identically or differently, by fluorine, chlorine or methyl,
and the salts thereof.

The present invention also relates to novel compounds of the general formula (I)

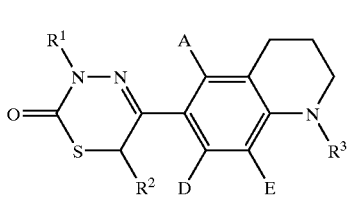

(I), in which
A, D, E and $R^1$ represent hydrogen,
$R^2$ represents methyl,
$R^3$ represents a radical of the formula $—X—R^4$,
in which
X represents CO or $SO_2$,
$R^4$ denotes a radical $—NH—(C_1–C_6$-alkyl) or a radical $—NH—(CH_2)_n—Ar$, in which n=0, 1 or 2, in particular in which n=0 or 1, where Ar in this case represents an optionally monosubstituted or polysubstituted aromatic ring or ring system, in particular phenyl or naphthyl, it being possible for the ring or the ring system optionally to contain one or more heteroatoms from the series N, S and/or O,
or
$R^4$ denotes an optionally monosubstituted or polysubstituted $(C_1–C_6)$-cycloalkyl radical, in particular an optionally substituted cyclopropyl or cyclohexyl radical, or represents an optionally substituted aromatic radical, in particular phenyl or naphthyl, or represents an optionally monosubstituted or polysubstituted benzyl radical, or else represents an optionally monosubstituted or polysubstituted phenoxy or benzyloxy radical,
or
$R^4$ denotes a radical $-(CH_2)_n—R^7$, in which n=0, 1 or 2, in particular n=0 or 1, where the radical $R^7$ denotes a 5- to 6-membered aromatic heterocycle having up to 3 ring heteroatoms from the series S, N and/or O, which heterocycle can, for its part, be optionally monosubstituted or polysubstituted,
or
$R^4$ denotes a $(C_1–C_3)$-alkyl radical which can be optionally substituted by $(C_6–C_{10})$-aryl, in particular phenyl or naphthyl, by phenoxy, by benzyloxy or by a 5- to 6-membered aromatic heterocycle having up to 3 ring heteroatoms from the series S, N and/or O, it being possible for the ring systems which are listed here to be optionally substituted, for their part, by substituents selected from the group consisting of halogen, nitro, trifluoromethyl, cyano, carboxyl, hydroxyl, trifluoromethoxy, (C$_1$–C$_6$)-alkylthio, (C$_1$–C$_6$)-alkoxy and (C$_1$–C$_6$)-alkoxycarbonyl, and the salts thereof.

The novel compounds are equally well suited for the abovementioned used.

The present invention relates, in particular, to novel compounds of the general formula (I)

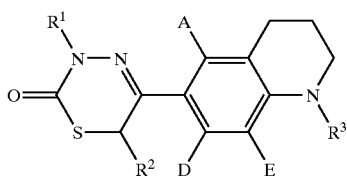

(I), in which

A, D, E and R$^1$ represent hydrogen,

R$^2$ represents methyl,

R$^3$ represents a radical of the formula —CO—R$^4$, in which

R$^4$ denotes one of the following radicals:

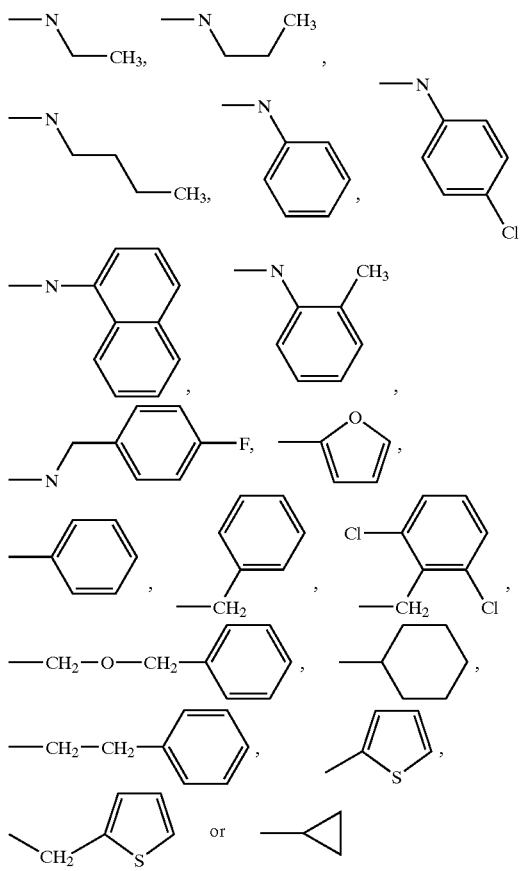

and the salts thereof.

The present invention consequently relates to the novel compounds which are listed in the following table A and which are equally well suited for the abovementioned use, a

function always being meant in the case of the structures which contain the

radical(s).

TABLE A

Structure

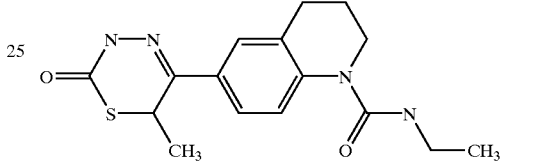

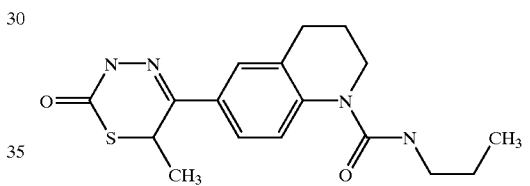

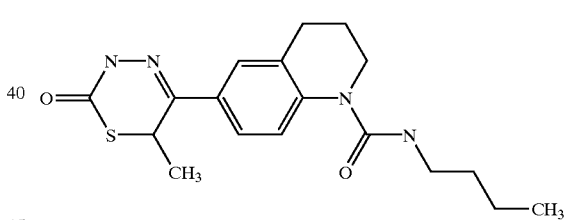

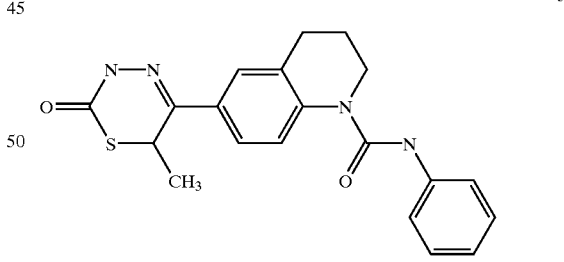

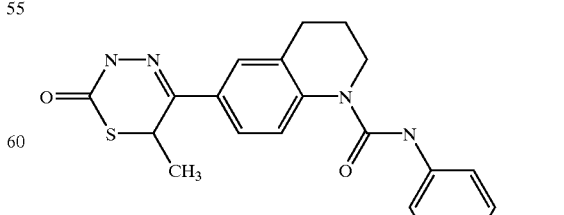

TABLE A-continued
Structure
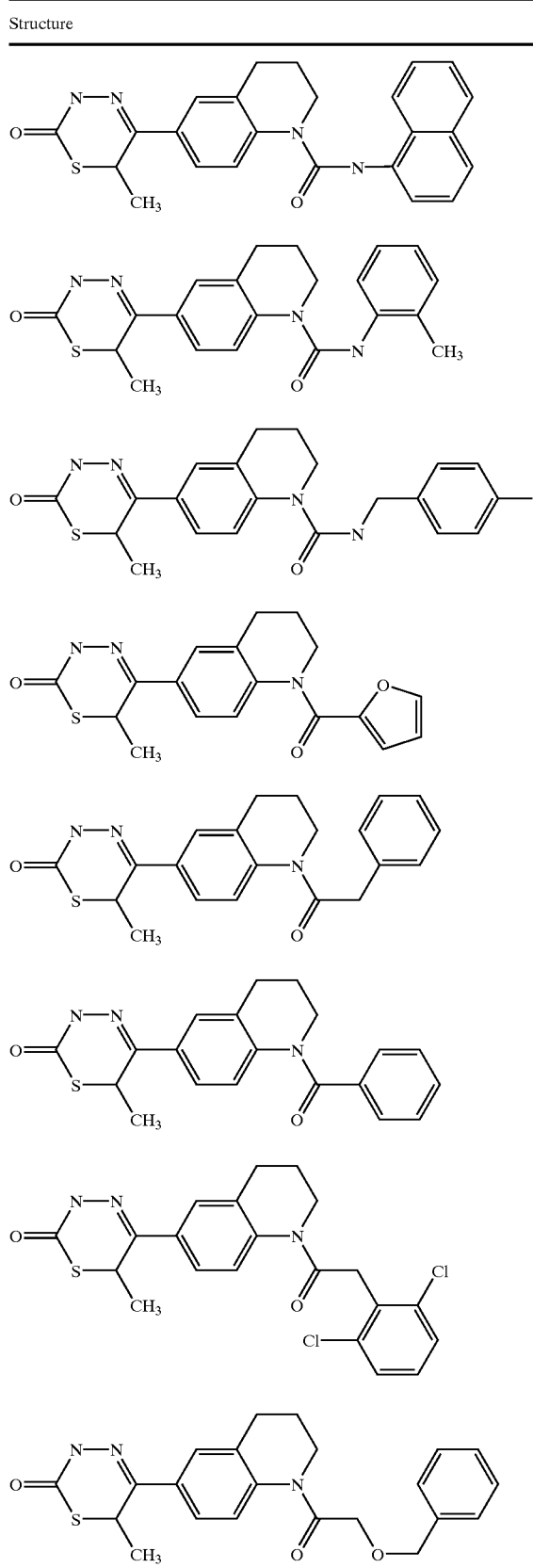
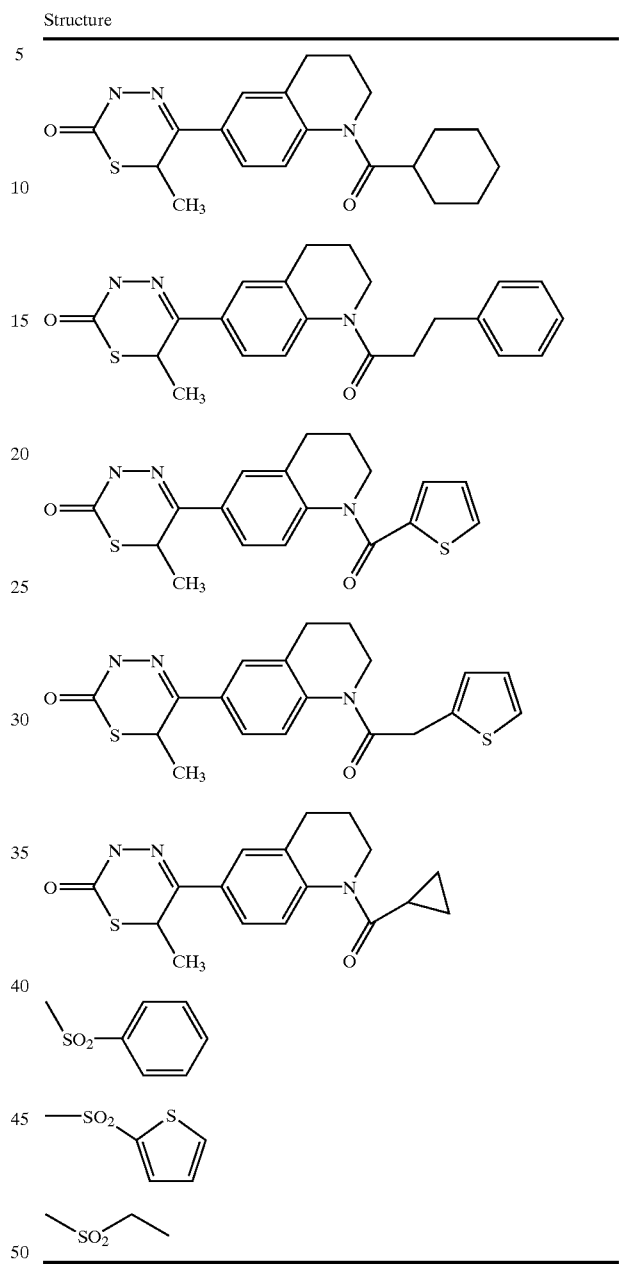
The present invention also relates to a process for preparing the compounds of the general formula (I), wherein compounds of the general formula (II)
(II),
in which
A, D, E, $R^1$ and $R^2$ have the abovementioned meaning, are reacted with compounds of the general formula (III)

R³—L (III)

in which
R³ has the abovementioned meaning
and
L represents halogen, and preferably represents chlorine,
in inert solvents, where appropriate in the presence of a base.

The process according to the invention can be explained, by way of example, by means of the following formula scheme:

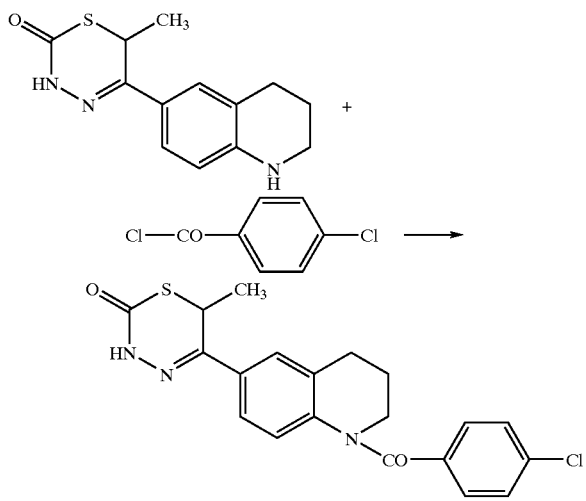

Suitable solvents in this connection are organic solvents which are inert under the reaction conditions. These include halogenohydrocarbons, such as dichloromethane, trichloromethane, tetrachloromethane, 1,2-dichloroethane, trichloroethane, tetrachloroethane, 1,2-dichloroethylene or trichloroethylene, hydrocarbons, such as benzene, xylene, toluene, hexane or cyclohexane, dimethylformamide, acetonitrile, THF, dioxane or dibutyl ether, acetone, and hexamethylphosphoric triamide. It is equally well possible to use mixtures of solvents. Dichloromethane and THF are particularly preferred.

Suitable bases are the customary inorganic or organic bases. These preferably include alkali metal hydroxides, such as sodium or potassium hydroxide, or alkali metal carbonates, such as sodium or potassium carbonate, or sodium or potassium methoxide or sodium or potassium ethoxide or potassium tert-butoxide, or amides, such as sodium amide, lithium bis(trimethylsilyl) amide or lithium diisopropylamide, or organometallic compounds, such as butyllithium or phenyllithium, and also organic bases, such as pyridine, triethylamine, DBU, DBN, dimethylaminopyridines, etc. Triethylamine and pyridine are preferred.

The base in this context can be used in the quantity of from 1 to 5 mol, preferably of from 1 to 2 mol, based on I mol of the compounds of the general formula (II).

In general, the reaction takes place in a temperature range of from −78° C. up to reflux temperature, preferably in a range from 0° C. to +50° C.

The reaction can be carried out under normal, increased or decreased pressure (e.g. in a range from 0.5 to 5 bar). In general, the reaction is carried out under normal pressure.

The compounds of the general formulae (II) and (III) are either known per se to the skilled person or can be prepared using customary methods.

The compounds of the general formula (I) which are in accordance with the invention and used in accordance with the invention exhibit a valuable pharmacological spectrum of activity which was not foreseeable and are particularly suitable, therefore, for the prophylaxis and/or treatment of diseases.

They can preferably be employed in pharmaceuticals for the prophylaxis and/or treatment of anemias, such as in premature baby anemias, in nephrogenic or renal ianemias, such as anemias associated with chronic renal insufficiency, in anemias following chemotherapy and in the anemia suffered by HIV patients, i.e. they can consequently be used, in particular, for treating severe anemias.

Even when the endogenous EPO production is completely intact, administration of the compounds according to the invention and used according to the invention can induce an additional stimulation of erythropoiesis, something which can be exploited, in particular, in the case of individuals donating their own blood.

All the customary administration forms are suitable for administering the compounds according to the invention and used according to the invention. The administration is preferably effected orally, transdermally or parenterally. Very particular preference is given to oral administration, which represents an additional advantage as compared with the therapy of anemias with rhEPO, as is known from the prior art.

The compounds according to the invention and used according to the invention act, in particular, as erythropoietin sensitizers. "Erythropoietin sensitizers" is the term used for compounds which are able to influence the action of the EPO which is present in the body so efficiently that erythropoiesis is increased and, in particular, oxygen supply is improved. Surprisingly, the compounds are also active orally, thereby substantially improving and simultaneously simplifying therapeutic use while excluding or reducing the known side-effects.

The present invention thus also relates to the use of the EPO sensitizers for stimulating erythropoiesis, in particular for the prophylaxis and/or treatment of anemias, preferably severe anemias, such as premature baby anemia, anemia associated with chronic kidney insufficiency, anemia following chemotherapy or else anemia in HIV patients. Particular preference is given to administering the so-called EPO sensitizers orally for the abovementioned purposes.

Thus, the compounds according to the invention and used according to the invention enable erythropoiesis to be stimulated efficiently and consequently make possible a prophylaxis and/or therapy of anemias which intervenes prior to the stage at which the conventional methods of treatment with EPO begin. This is because the compounds according to the invention and used according to the invention enable the endogenous EPO to be influenced effectively, thereby making it possible to avoid direct administration of EPO together with the disadvantages associated therewith.

The present invention consequently also relates to medicaments and pharmaceutical compositions which comprise at least one compound of the general formula (I) according to the invention and used according to the invention together with one or more pharmacologically harmless auxiliary or carrier substances, and also to their use for stimulating erythropoiesis, in particular for the purposes of prophylaxis and/or treatment of anemias, such as premature baby anemia, anemias associated with chronic renal insufficiency, anemias following chemotherapy or anemias in HIV patients.

The present invention will be illustrated by the following examples, which do not, however, limit the invention in any way.

A ASSESSMENT OF PHYSIOLOGICAL EFFICACY

1. General test Methods a) Test Description (in vitro)

Proliferation of Human Erythrocytic Precursor Cells 20 ml of heparinized blood were diluted with 20 ml of PBS (phosphate-buffer saline) and centrifuged for 20 min (220×g). The supernatant was discarded and the cells were resuspended in 30 ml of PBS and pipetted onto 17 ml of Ficoll Paque® (d=1.077 g/ml, Pharmacia) in a 50 ml tube. The samples were centrifuged at 800×g for 20 min. The mononuclear cells at the boundary layer were transferred into a new centrifuge tube, diluted with 3 times the volume of PBS and centrifuged at 300×g for 5 min. The CD34-positive cells from this cell fraction were isolated using a commercial purification method (CD34 Multisort Kit supplied by Miyltenyi). The CD34-positive cells (6000–10000 cells/ml) were resuspended in stem cell medium (0.9% methyl cellulose, 30% calf serum, 1% albumin (bovine), 100 $\mu$M 2-mercaptoethanol and 2 mM L-glutamine) supplied by StemCell Technologies Inc. 10 mU of human erythropoietin/ml, 10 ng of human IL-3 (interleukin-3)/ml and 0–10 $\mu$M test substance were added. 500 $\mu$l were 35 cultured per well (microtiter plates in each case containing 24 wells) at 37° C. for 14 days and in 5% $CO_2$/95% air.

The cultures were diluted with 20 ml of 0.9% w/v NaCl solution, centrifuged at 600×g for 15 min and resuspended in 200 $\mu$l of 0.9% w/v NaCl. In order to determine the number of erythrocytic cells, 50 $\mu$l of the cell suspension were pipetted into 10 $\mu$l of benzidine staining solution (20 $\mu$g of benzidine in 500 $\mu$l of DMSO, 30 $\mu$l of $H_2O_2$ and 60 $\mu$l of concentrated acetic acid). The number of blue cells was counted with the aid of a microscope.

When the test substances are added, a significant increase in the proliferation of erythrocytic precursor cells is observed according to the present invention in each case.

b) Test Description, Mouse Hematocrit

Normal mice are treated with test substances over several days. The test substances are administered intraperitoneally, subcutaneously or orally. Preferred solvents are Solutol/DMSO/sucrose/NaCl solution or Glycofurol.

From day 0 (prior to the first administration), up to approx. 3 days after the last administration, approx. 70 $\mu$l of blood are withdrawn on several occasions by puncturing the retroorbital venus plexus with a hematocrit capillary. The samples are centrifuged and the hematocrit is determined by reading off manually. The primary parameter is the increase in hematocrit, in relation to the starting value, in the treated animals as compared with the change in the hematocrit in the placebo control (doubly standardized value).

The test substances according to the present invention which are administered lead to a significant increase in the hematocrit.

The active compounds according to the invention and used according to the invention can be convened, in a known manner, into the customary formulations, such as tablets, coated tablets, pills, granules, aerosols, syrups, emulsions, suspensions and solutions, using inert, nontoxic, pharmaceutically suitable carrier substances or solvents. In this connection, the therapeutically active compound should in each case be present at a concentration of from about 0.5 to 90% by weight of the total mixture, i.e. in quantities which are sufficient for achieving the given dosing latitude.

The formulations are prepared, for example, by extending the active compounds with solvents and/or carrier substances, where appropriate using emulsifying agents and/or dispersing agents, it being possible, for example when using water as a diluent, to use organic solvents as auxiliary solvents, where appropriate.

Administration is effected in a customary manner, preferably orally, transdermally or parenterally, in particular perlingually or intravenously. In general, it has proved to be advantageous, when administering intravenously, to administer quantities of from about 0.01 to 10 mg/kg, preferably of from about 0.1 to 10 mg/kg, of bodyweight in order to achieve effective results.

Despite this, it can be necessary, where appropriate, to diverge from the quantities mentioned, specifically in dependence on bodyweight or on the nature of the administration route, on the individual reaction to the drug, on the type of formulation and on the time or interval at which the administration takes place. Thus, it can be sufficient, in some cases, to make do with less than the previously mentioned lowest quantity while, in other cases, it is necessary to exceed the abovementioned upper limit. When relatively large quantities are being administered, it can be advisable to divide these quantities into several single doses which are then given during the course of the day.

B PREPARATION EXAMPLES

Example 1

5-(1-Thiophene-2-carbonyl -1,2,3,4-tetrahydroquinolin-6-yl)-6-methyl-3,6-dihydro-1,3-4-thiadiazin-2-one

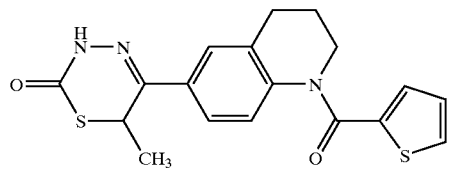

130.7 mg (0.5 mmol) of 5-(1,2,3,4-tetrahydroquinolin-6-yl)-6-methyl-3,6-dihydro-1,3-4-thiadiazin-2-one are dissolved in 5 ml of dioxane, and 63.8 mg (0.75 mmol) of pyridine and 113.4 mg (0.75 mmol) of thiophene-2-carbonyl chloride are then added consecutively. The mixture is stirred at 20° C. for 30 minutes and then diluted with acetic acid; it is then washed with 0.5 N hydrochloric acid, with water, with sodium hydrogencarbonate solution and once again with water, after which it is dried and inspissated. 110 mg (59%) of crystals having a melting point of 190–191° C. are obtained from a little ethyl acetate.

The compounds listed in the following table were prepared in analogy with the above directions.

The abbreviation (D) given in connection with the melting point denotes decomposition.

| Ex. | Structure | MW | Yield (% of theory) | Mp.: (° C.) | Rf value, TLC aluminium roll silica gel |
|---|---|---|---|---|---|
| 2 | 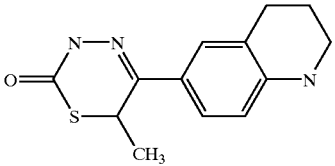 | 261.35 | 51 | 176–8 | |
| 3 | 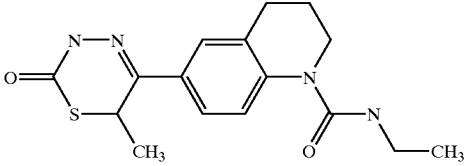 | 332.43 | 43 | 122–4 (D) | |
| 4 | 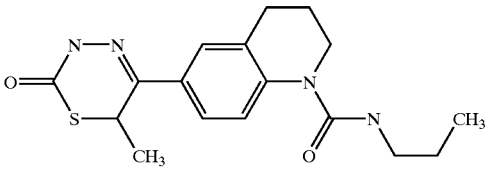 | 346.45 | 80 | 151–3 | |
| 5 | 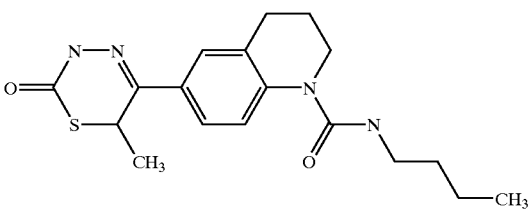 | 360.48 | 75 | 133–4 | |
| 6 | 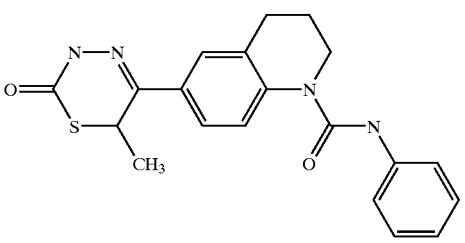 | 380.47 | 75 | 213–4 (D) | |
| 7 | 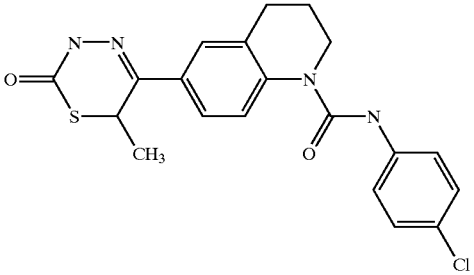 | 414.92 | | 218–20 (D) | |
| 8 | 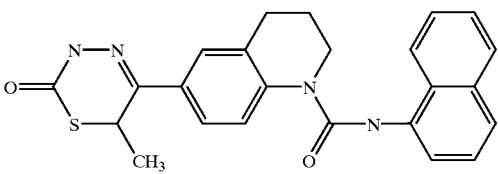 | 430.53 | 62 | 165–6 (D) | |

-continued
| Ex. | Structure | MW | Yield (% of theory) | Mp.: (° C.) | Rf value, TLC aluminium roll silica gel |
|---|---|---|---|---|---|
| 9 | 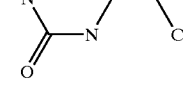 | 394.50 | 80 | 153–4 | |
| 10 | 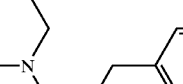 | 412.49 | 62 | 158–60 | |
| 11 | 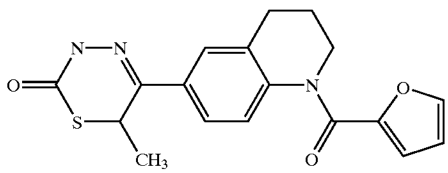 | 355.42 | 43 | 159–61 | |
| 12 | 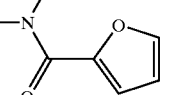 | 379.48 | 63 | | 0.18 |
| 13 | 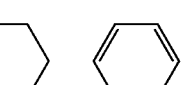 | 365.46 | 68 | 202–4 | |
| 14 | 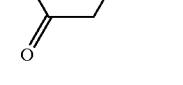 | 448.37 | 25 | 188–189 | |
| 15 | 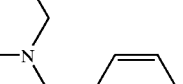 | 409.51 | 81 | | 0.11 |
| 16 | 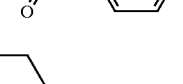 | 371.51 | 89 | 148–50 (D) | |

-continued

| Ex. | Structure | MW | Yield (% of theory) | Mp.: (° C.) | Rf value, TLC aluminium roll silica gel |
|---|---|---|---|---|---|
| 17 | 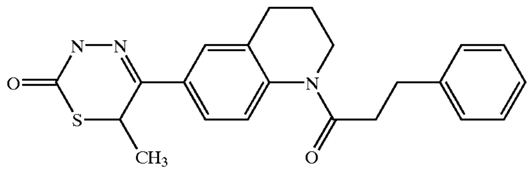 | 393.51 | 43 | 172–4 | |
| 18 | 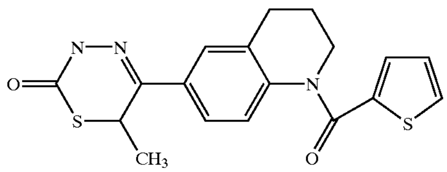 | 371.48 | 59 | 190–1 | |
| 19 | 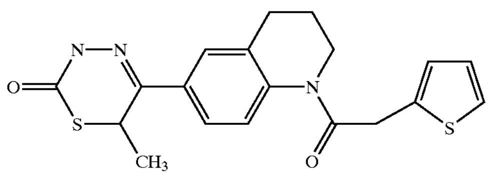 | 385.51 | 36 | | 0.19 |
| 20 | 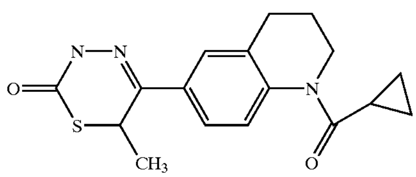 | 329.42 | 99 | | 0.16 |
| 21 | 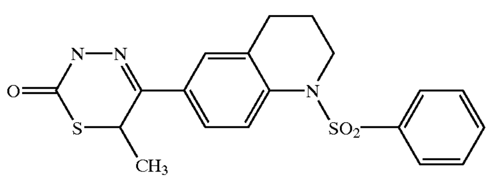 | | | 167–169 | (TLC in Tol/EA 4:1) |
| 22 | 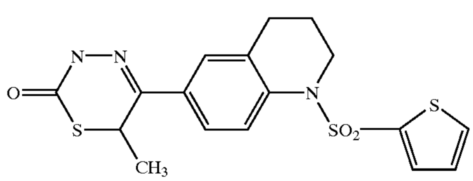 | | | 165–169 | |
| 23 | 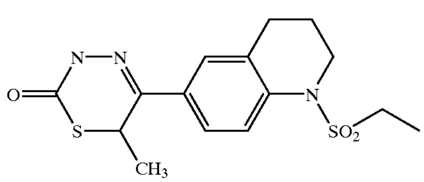 | | | | 0.42 (TLC in Tol/EA 2:1) |

What is claimed is:

1. A method for treatment of anemias, comprising administering an effective amount of a tetrahydroquinolinyl-6-methyldihydrothiadiazinone of formula (I)

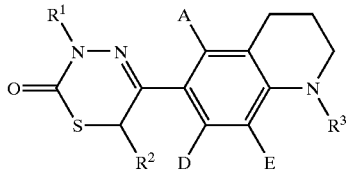

in which
A, D and E are identical or different and represent hydrogen, halogen, trifluoromethyl or hydroxyl or represent $(C_1-C_6)$-alkyl or represent $(C_1-C_6)$-alkoxy,
$R^1$ and $R^2$ are identical or different and represent hydrogen or represent $(C_1-C_6)$-alkyl,
$R^3$ represents a radical of the formula $—(X)_a—R^4$,
in which
X represents CO or $SO_2$,
a denotes a number 0 or 1,
and
$R^4$ denotes $(C_3-C_8)$-cycloalkyl or $(C_6-C_{10})$-aryl or a 5- to 6-membered aromatic heterocycle having up to 3 ring heteroatoms from the series S, N and/or O, it being possible for the ring systems which are listed here to be optionally substituted up to 3 times, identically or differently, by substituents selected from the group consisting of: halogen, trifluoromethyl, nitro, hydroxyl, carboxyl, $(C_1-C_6)$-alkyl, $(C_1-C_6)$-alkoxy and $(C_1-C_6)$-alkoxycarbonyl,
or
$R^4$ denotes $(C_1-C_8)$-alkyl which is optionally substituted by $(C_6-C_{10})$-aryl, phenoxy or benzyloxy or by a 5- to 6-membered aromatic heterocycle having up to 3 ring heteroatoms from the series S, N and/or O, it being possible for the ring systems which are listed here to be optionally substituted, up to 4 times, identically or differently, by substituents selected from the group halogen, nitro, trifluoromethyl, cyano, carboxyl, hydroxyl, trifluoromethoxy, $(C_1-C_6)$-alkylthio, $(C_1-C_6)$-alkoxy and $(C_1-C_6)$-alkoxycarbonyl,
or
$R^4$ denotes a radical of the formula $—CO—NR^5R^6$,
in which
$R^5$ and $R^6$ are identical or different and denote hydrogen or $(C_1-C_6)$-alkyl which is optionally substituted by $(C_6-C_{10})$-aryl which, for its part, can be substituted, once to twice, identically or differently, by halogen or $(C_1-C_6)$-alkyl, or
denote $(C_6-C_{10})$-aryl which can be optionally substituted, once to three times, identically or differently, by halogen, nitro, cyano, $(C_1-C_6)$-alkyl, $(C_1-C_6)$-alkoxy or hydroxyl,
or a pharmaceutically acceptable salt thereof.

2. The method as claimed in claim 1, where, in formula (I),
A, D and E are identical or different and represent hydrogen, fluorine, chlorine, bromine or hydroxyl, or represent $(C_1-C_4)$-alkyl or represent $(C_1-C_4)$-alkoxy,
$R^1$ and $R^2$ are identical or different and represent hydrogen, methyl or ethyl,
$R^3$ represents a radical of the formula $—(X)_a—R^4$,
in which
X represents CO or $SO_2$,
a denotes a number 0 or 1,
and
$R^4$ denotes cyclopropyl, cyclopentyl, cyclohexyl or cyclohepyl, or denotes phenyl, phenoxy, naphthyl, pyridyl, pyrimidyl, pyridazinyl, thienyl, furyl, imidazolyl or pyrryl which can each be optionally substituted, up to 3 times, identically or differently, by substituents selected from the group consisting of fluorine, chlorine, bromine, $(C_1-C_4)$-alkyl, $(C_1-C_4)$-alkoxy and hydroxyl,
or
$R^4$ denotes $(C_1-C_6)$-alkyl which is optionally substituted by phenyl, phenoxy, benzyloxy, naphthyl, pyridyl, pyrimidyl, pyridazinyl, thienyl or furyl, which, for their part, can optionally be substituted, up to 4 times, identically or differently, by substituents selected from the group consisting of fluorine, chlorine, bromine, nitro, trifluoromethyl, cyano, trifluoromethoxy, hydroxyl, $(C_1-C_4)$-alkoxy and $(C_1-C_4)$-alkyl,
or
$R^4$ denotes a radical of the formula $—CO—NR^5R^6$,
in which
$R^5$ and $R^6$ are identical or different and denote hydrogen or denote $(C_1-C_4)$-alkyl which is optionally substituted by phenyl or fluorine, or
denote naphthyl or phenyl which are each optionally substituted, up to 2 times, identically or differently, by fluorine, chorine or $(C_1-C_3)$-alkyl.

3. The method as claimed in claim 1, where, in formula (I),
A, D and E are identical or different and represent hydrogen, fluorine, chlorine or $(C_1-C_3)$-alkyl,
$R^1$ and $R^2$ are identical or different and represent hydrogen or methyl,
$R^3$ represents a radical of the formula $—(X)_a—R^4$,
in which
X represents CO or $SO_2$,
a denotes a number 0 or 1,
and
$R^4$ denotes cycloalkyl or cyclohexyl or denotes phenyl or pyridyl which can each be optionally substituted, up to 2 times, identical or differently, by substituents selected from the group consisting of fluorine, chlorine, bromine, $(C_1-C_3)$-alkyl and $(C_1-C_4)$-alkoxy,
or
$R^4$ denotes $(C_1-C_4)$-alkyl which is optionally substituted by phenyl, pyridyl, pyrimidyl or pyridazinyl which are each optionally substituted, up to 2 times, identically or differently, by substituents selected from the group consisting of fluorine, chorine, bromine, nitro, cyano, hydroxyl, trifluoromethyl, trifluoromethoxy, $(C_1-C_3)$-alkylthio, $(C_1-C_3)$-alkyl and $(C_1-C_3)$-alkoxy,
or
$R^4$ denotes a radical of the formula $—CO—NR^5R^6$,
in which
$R^5$ and $R^6$ are identical or different and denote hydrogen or denote $(C_1-C_3)$-alkyl which is optionally substituted by phenyl or fluorine or
denote phenyl or naphthyl which are each optionally substituted, once to twice, identically or differently, by fluorine, chlorine or methyl.

4. A tetrahydroquinolinyl-6-methyldihydrothiadiazone derivative of formula (I), (I), in which
A, D, E and $R^1$ represent hydrogen,
$R^2$ represents methyl,
and
$R^3$ represents a radical of the formula —X—$R^4$,
 in which
 X represents CO or $SO_2$,
 $R^4$ denotes a radical —NH—($C_1$–$C_6$-alkyl) or a radical —NH—$(CH_2)_n$—Ar, in which n=0, 1 or 2, where Ar in this case represents an optionally monosubstituted or polysubstituted aromatic ring or ring system, the ring or the ring system optionally containing one heteroatom independently selected from the group consisting of N, S, and O,
 or
 $R^4$ denotes an optionally monosubstituted or polysubstituted ($C_1$–$C_6$)-cycloalkyl radical, or represents an optionally substituted aromatic radical, or represents an optionally monosubstituted or polysubstituted benzyl radical, or else represents an optionally monosubstituted or polysubstituted phenoxy or benzyloxy radical,
 or
 $R^4$ denotes a radical —$(CH_2)_n$—$R^7$, in which n=0, 1 or 2, where the radical $R^7$ denotes a 5- to 6-membered aromatic heterocycle having up to 3 ring heteroatoms independently selected from the group consisting of N, O, and S, which heterocycle can, for its part, be optionally monosubstituted or polysubstituted,
 or
 $R^4$ denotes a ($C_1$–$C_3$)-alkyl radical which can be optionally substituted by ($C_6$–$C_{10}$)-aryl, by phenoxy, by benzyloxy or by a 5- to 6-membered aromatic heterocycle having up to 3 ring heteroatoms independently selected from the group consisting of S, N, and O, the ring systems listed here being optionally substituted, for their part, by substituents selected from the group consisting of halogen, nitro, trifluoromethyl, cyano, carboxyl, hydroxyl, trifluoromethoxy, ($C_1$–$C_6$)-alkylthio, ($C_1$–$C_6$)-alkoxy and ($C_1$–$C_6$)-alkoxycarbonyl,
or a pharmaceutically acceptable salt thereof.

5. A teterahydroquinolinyl-6-methyldihydrothiadiazinone derivative of formula (I), (I), in which A, D, E and $R^1$ represent hydrogen,
$R^2$ represents methyl,
and
$R^3$ represents a radical of the formula —CO—$R^4$,
 in which
 $R^4$ is a radical selected from the group consisting of or a pharmaceutically acceptable salt thereof.

6. A method for treatment of anemias comprising administering an effective amount of a tetrahydroquinolinyl-6-methyldihydrothiadiazinone derivative as claimed in claim 4.

7. The method for treatment of anemias as claimed in claim 1, 2, 3, 6, or 11, wherein the anemias to be treated are premature baby anemias, anemias associated with chronic renal insufficiency, anemias following chemotherapy or anemias in HIV patients.

8. The method for treatment of anemias as claimed in claim 1, 2, 3, 6, or 11, wherein the anemia results from individuals donating their own blood and the treatment is to stimulate erythropoiesis.

9. A process for preparing tetrahydroquinolinyl-6-methyldihydrothiadiazinones of formula (I), (I), characterized in that compounds of the formula (II)

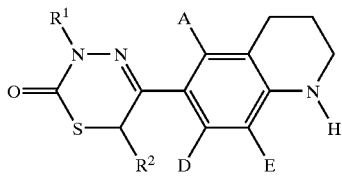

(II), in which
A, D, E, $R^1$ and $R^2$ have the meaning defined in claim 1, are reacted with compounds of the formula (III)

$$R^3-L \qquad \text{(III)}$$

in which
$R^3$ has the meaning defined in claim 1,
and
L represents halogen,
in an inert solvent, where appropriate in the presence of a base.

10. A pharmaceutical composition which comprises one or more tetrahydroquinolinyl-6-methyldihydrothiadiazinone compounds of formula (I) and also one or more pharmacologically inert auxiliary and carrier substances.

11. A method for treatment of anemias comprising administering an effective amount of a tetrahydroquinolinyl-6-methyldihydrothiadiazinone derivative as claimed in claim 5.

12. The process of claim 9 wherein L is chlorine.

13. The method of claim 1 wherein $R^1$ and $R^2$ are $(C_1-C_4)$-alkyl.

14. The compound of claim 4 wherein when $R^4$ is $-NH(CH_2)_n-Ar$, the subscript n is 0 or 1.

15. The compound of claim 4 wherein when $R^4$ is $-NH(CH_2)_n-Ar$, the group Ar is phenyl or naphthyl.

16. The compound of claim 4 wherein when $R^4$ is a $(C_1-C_6)$-cycloalkyl radical, it is an optionally substituted cyclopropyl or cyclohexyl radical.

17. The compound of claim 4 wherein when $R^4$ is an aromatic radical, it is optionally substituted phenyl or napthyl.

18. The compound of claim 4 wherein when $R^4$ is $-(CH_2)_n-R^7$, the subscript n is O or 1.

19. The compound of claim 4 wherein when $R^4$ is $(C_1-C_3)$-alkyl optionally substituted by $(C_6-C_{10})$-aryl, the optional substituent is phenyl or naphthyl.

* * * * *